US00PP37387P3

(12) United States Plant Patent
Boches et al.

(10) Patent No.: US PP37,387 P3
(45) Date of Patent: Apr. 28, 2026

(54) BLUEBERRY PLANT NAMED 'FCE18-015'

(50) Latin Name: *Ericaceae Vaccinium corymbosum*
Varietal Denomination: FCE18-015

(71) Applicant: Fall Creek Farm and Nursery, Inc., Lowell, OR (US)

(72) Inventors: Peter Stefan Boches, Hilo, HI (US); Antonio A. Alamo Bermudo, Seville (ES)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 19/063,460

(22) Filed: Feb. 26, 2025

(65) Prior Publication Data

US 2025/0280745 P1 Sep. 4, 2025

Related U.S. Application Data

(60) Provisional application No. 63/560,882, filed on Mar. 4, 2024.

(51) Int. Cl.
*A01H 5/08* (2018.01)
*A01H 6/36* (2018.01)

(52) U.S. Cl.
USPC ..... Plt./157
CPC ..... *A01H 6/368* (2018.05); *A01H 5/08* (2013.01)

(58) Field of Classification Search
USPC ..... Plt./156, 157
See application file for complete search history.

(56) References Cited

U.S. PATENT DOCUMENTS

| | | | |
|---|---|---|---|
| PP24,606 | P3 | 7/2014 | Brazelton et al. |
| PP27,771 | P2 | 3/2017 | Lyrene et al. |
| PP29,287 | P3 | 5/2018 | Brazelton et al. |
| PP29,468 | P3 | 7/2018 | Brazelton et al. |
| PP32,219 | P2 | 9/2020 | NeSmith |

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

The new blueberry plant variety 'FCE18-015' is provided. 'FCE18-015' is a commercial variety intended for the hand harvest fresh market. The variety is produced from a cross of 'FL06-556' (female parent, U.S. Plant Pat. No. 27,771) and 'Ventura' (male parent, U.S. Plant Pat. No. 24,606), which can be distinguished by its features. Plants of the new variety are vigorous with an upright shape. The fruit produced by the new variety has long-term storage capabilities.

7 Drawing Sheets

Latin name of the family, genus, and species:
Family—*Ericaceae.*
Genus—*Vaccinium.*
Species—*corymbosum.*
Variety denomination: The new blueberry plant claimed is of the variety denominated 'FCE18-015'.

STATEMENT REGARDING FEDERALLY-SPONSORED RESEARCH AND DEVELOPMENT

None.

BACKGROUND OF THE INVENTION

The present invention relates to a new and distinct cultivar blueberry plant (*Vaccinium corymbosum* L.), referred to as 'FCE18-015', herein described and illustrated. The new blueberry plant named 'FCE18-015' is a commercial variety.

Pedigree and History: The new blueberry plant originated from a cross of 'FL06-556' (female parent, U.S. Plant Pat. No. 27,771) and 'Ventura' (male parent, U.S. Plant Pat. No. 24,606). The cross that produced 'FCE18-015' was completed in Oregon in 2016. The seeds resulting from the above cross were sown and small plants were obtained which were physically and biologically different from each other. Selective study resulted in the identification of a single plant of the new variety. The new variety 'FCE18-015' was planted in 2017 in Spain; and selected in 2018 in Spain.

'FCE18-015' has been found to undergo asexual propagation techniques in Spain, such as in vitro propagation, through tissue culture. Asexual propagation techniques in Spain, have shown that the characteristics of the new variety are homogenous, stable, and strictly transmissible by such asexual propagation from one generation to another. Accordingly, the new variety undergoes asexual propagation in a true-to-type manner.

SUMMARY OF THE INVENTION

'FCE18-015' was selected because it has an exceptional plant habit and fruit quality. The plants are vigorous and healthy with an upright shape. The new variety produces fruit from both primocane and floricane buds. The fruit has a slight oblate to round shape and light blue color with a small dry scar ideal for long-term storage. The fruit is very firm, meaty and crunchy with a balanced sweetness to acidity ratio. This variety has superior long-term storage capabilities of up to 60 days while maintaining premium fruit quality.

The following characteristics of the new cultivar have been repeatedly observed and it was found that the new blueberry plant variety 'FCE18-015' possesses the following combination of characteristics:

1. Forming vigorous and upright shape.
2. Providing excellent shelf life, holding fruit quality up to 45 to 60 days based on cooler tests.
3. Exhibiting very firm fruit, having a consistent small dry scar and light blue color.

The new variety of the present invention can readily be distinguished from its ancestors. More specifically, 'FCE18-015' differs from both the female parent and the male parent because the fruit of the new variety maintains marketable fruit quality in cold storage for a longer period of time. Moreover, the new variety can be readily distinguished from other similar non-parental varieties. For example, 'FCM12-087' (U.S. Plant Pat. No. 29,287) provides a medium vigor plant and exhibits a late production of crop, whereas the new variety provides a medium to high vigor plant and exhibits a mid-production of crop.

BRIEF DESCRIPTION OF THE DRAWINGS

The accompanying photographic illustration shows typical specimens in full color of the foliage and fruit of the new variety 'FCE18-015'. The colors are as nearly true as is reasonably possible in a color representation of this type. The colors in the photographs are as accurate as possible with the photographic and printing technology utilized. The color values cited in the detailed botanical description accurately describe the colors of the new blueberry.

DETAILED BOTANICAL DESCRIPTION

Figure 1:
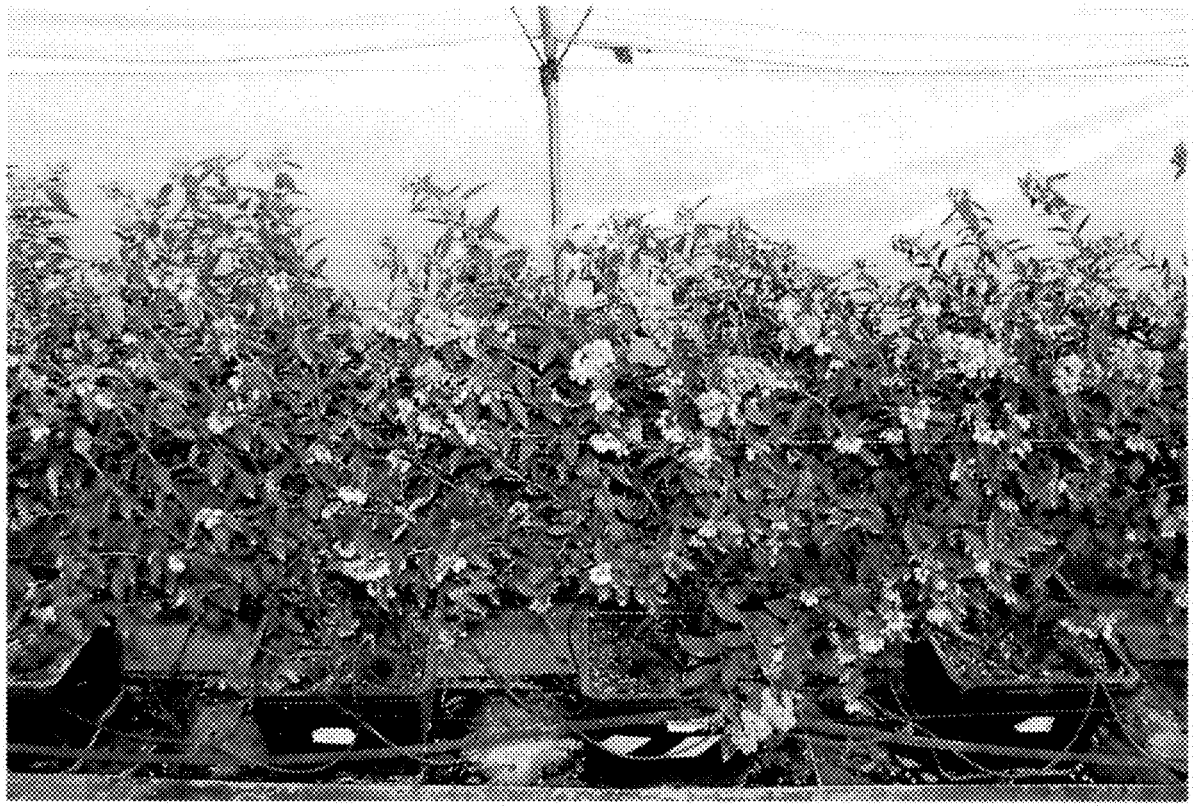
FIG. 1—depicts a mature plant of the new variety at beginning of the fruit maturity period, FIG. 2—depicts a mature plant of the new variety prior to fruiting, with a white background showing the structure of the plant.
Figure 2:
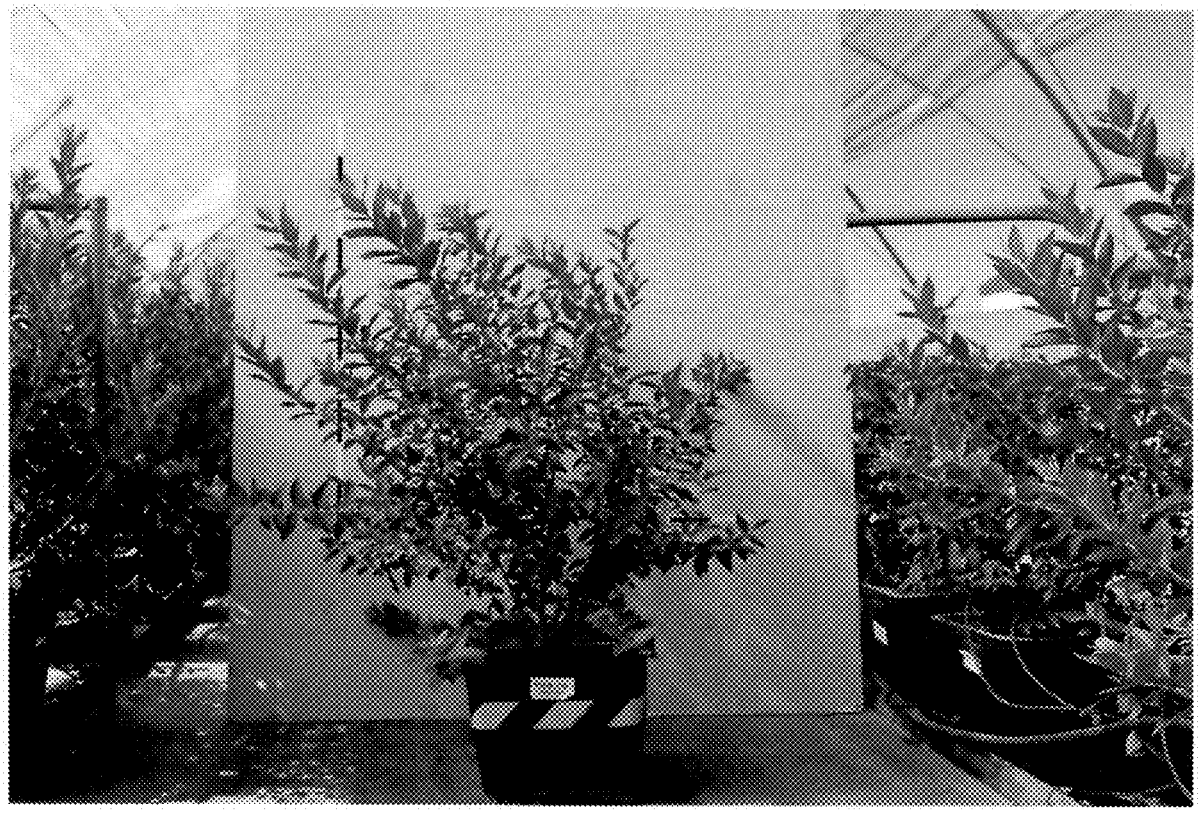
Figure 3:
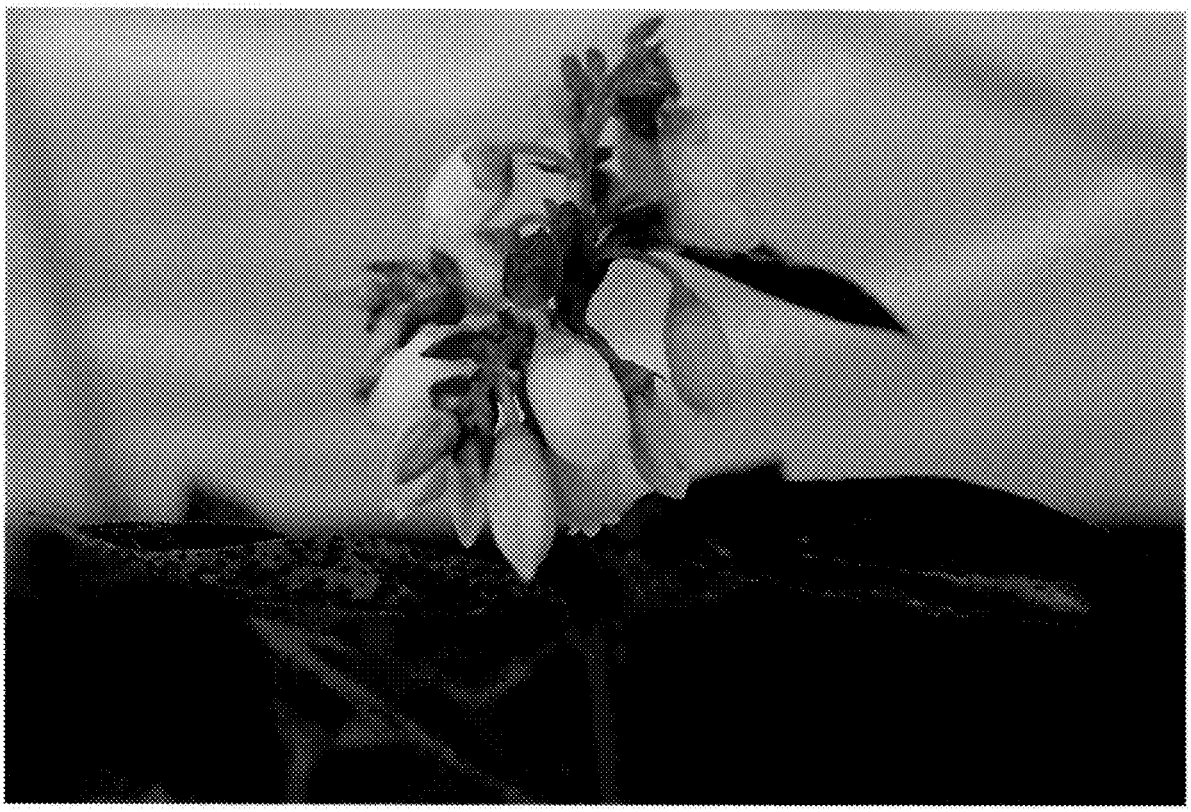
FIG. 3—depicts flowers of the new variety.
Figure 4:
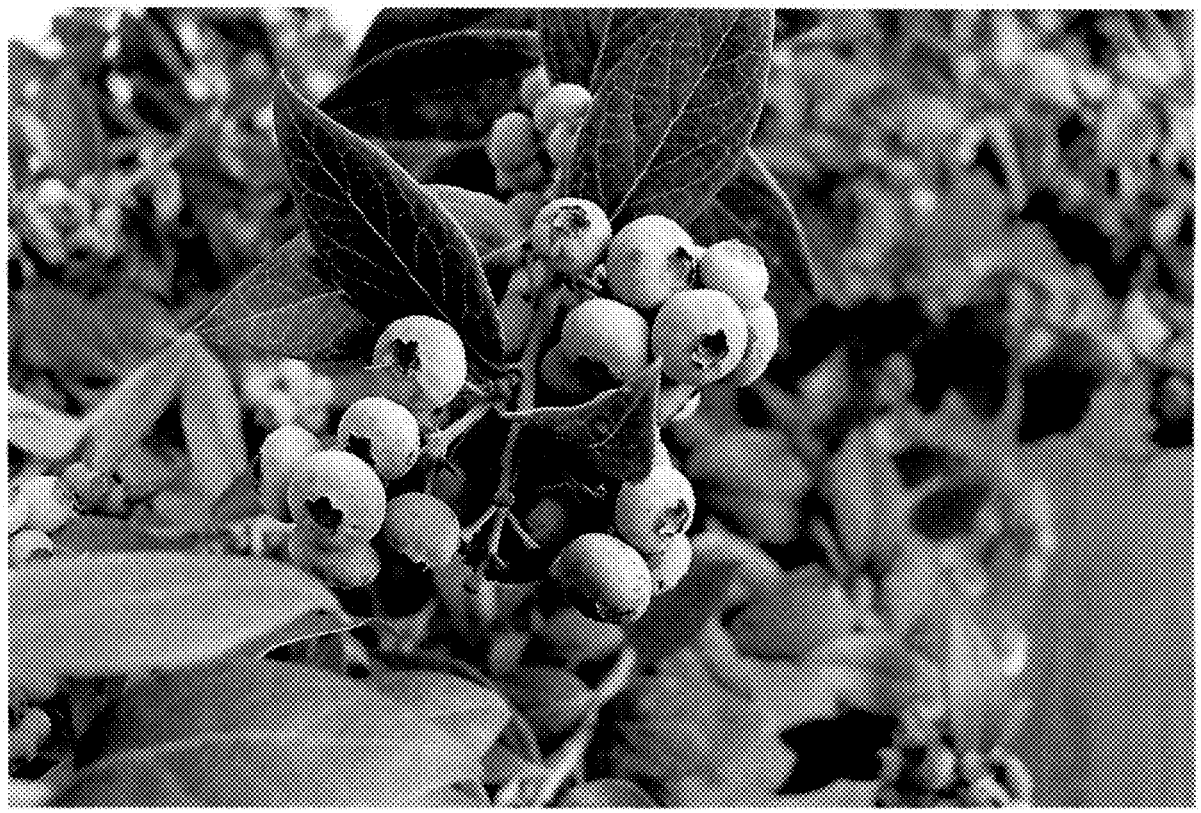
FIG. 4—depicts ripe fruit on the plant of the new variety.
Figure 5:
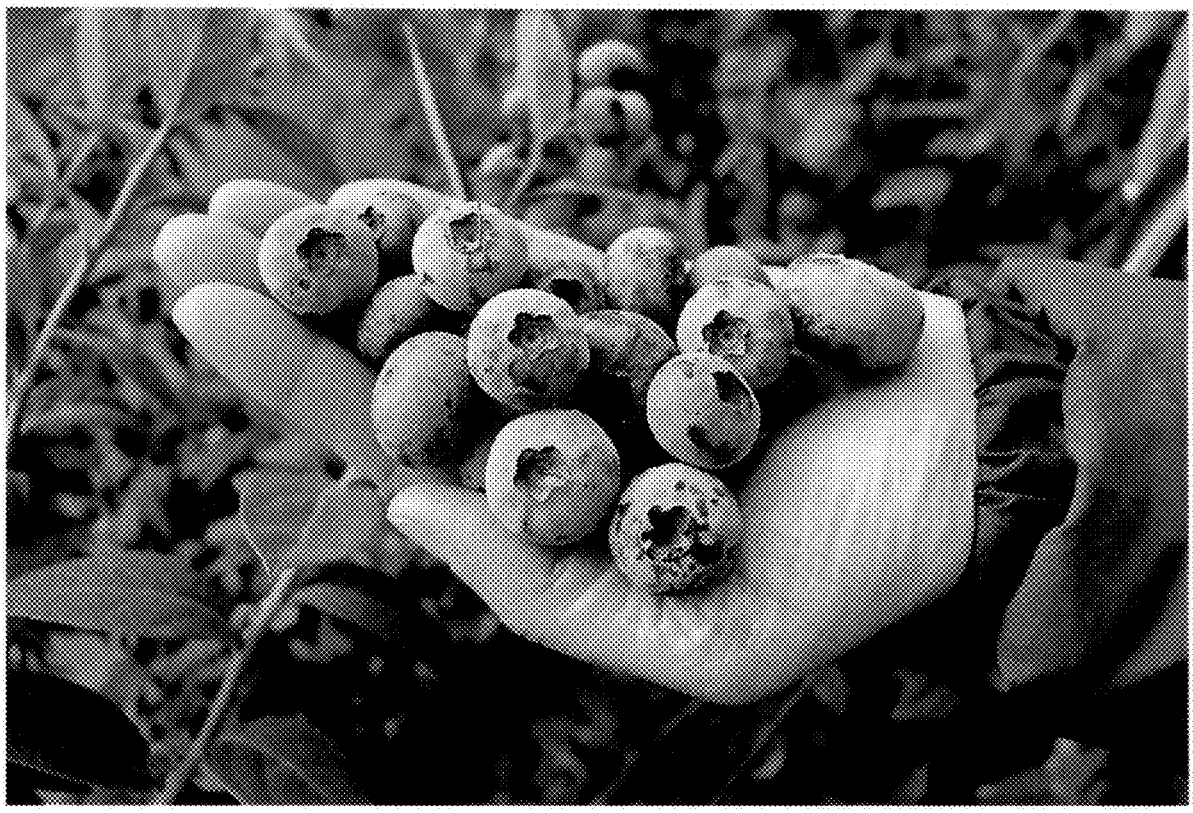
FIG. 5—depicts a handful of ripe fruit of the new variety.
Figure 6:
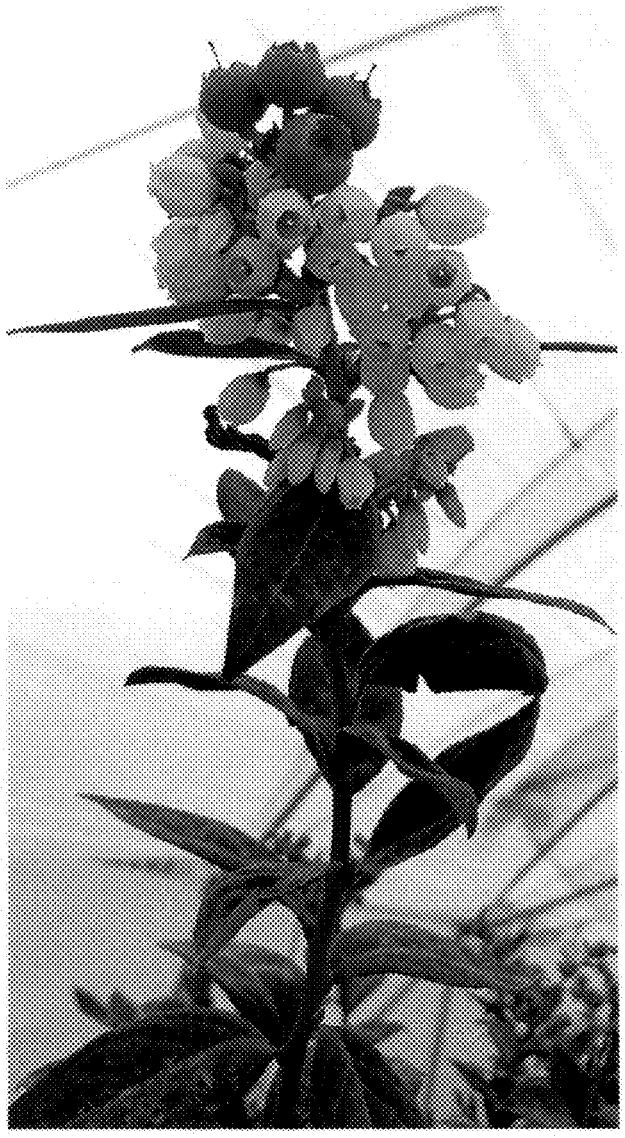
FIG. 6—depicts flowers and unripe fruit on a shoot of the new variety.
Figure 7:
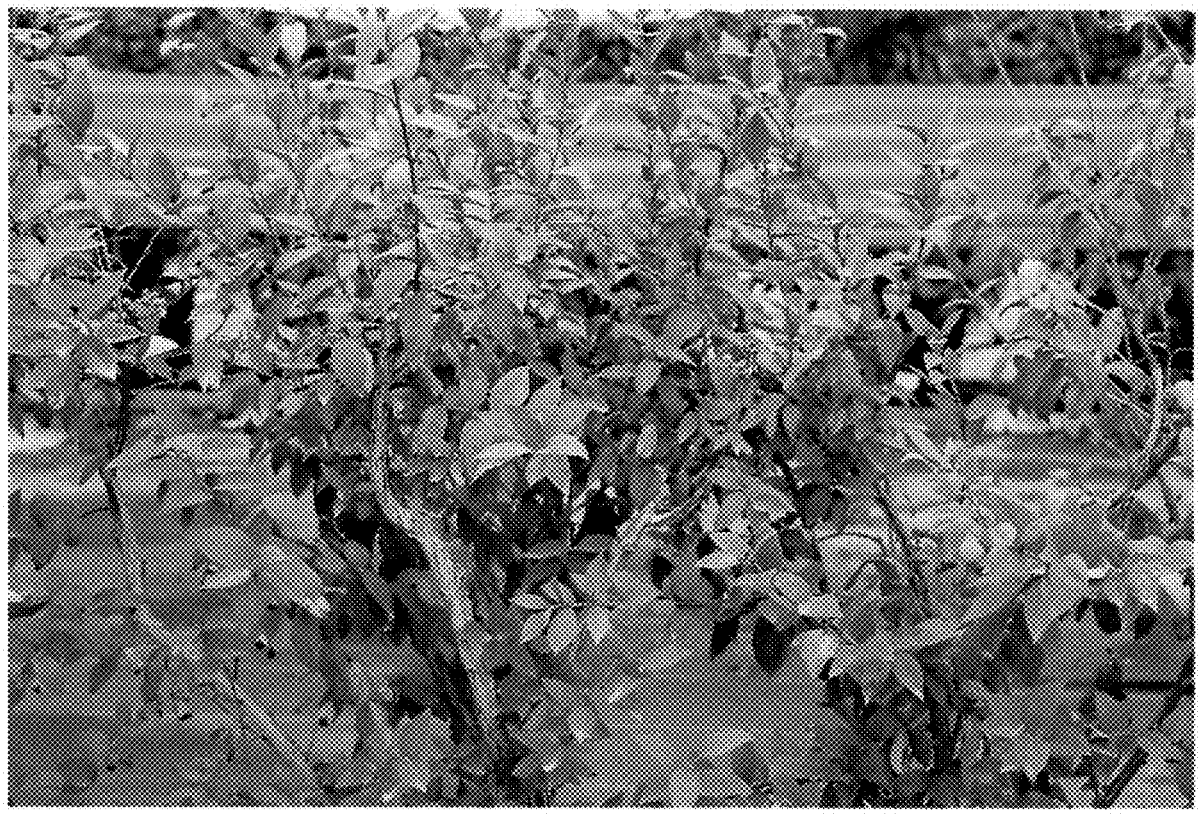
FIG. 7—depicts a mature plant of the new variety during the fall, showing the fall leaf colors.

The following detailed description sets forth the distinctive characteristics of 'FCE18-015'. The data which defines these characteristics was collected from asexual reproductions of the original selection. Dimensions, sizes, colors, and other characteristics are approximations and averages set forth as accurately as possible. The plant history was taken on plants approximately 3 to 4 years of age, and the descriptions relate to plants grown in the field in Spain, Seville, Villamanrique de la Condesa. Descriptions of fruit characteristics were made on fruit grown in Spain, Seville, Villamanrique de la Condesa. Color designations are from "The Pantone Book of Color" (by Leatrice Eiseman and Lawrence Herbery, Harry N. Abrams, Inc., Publishers, New York 1990) unless noted otherwise and the color designations used herein represent the closest color observed on the majority of the specified botanical feature. Where the Pantone color designations differ from the colors in the photographs, the Pantone colors are accurate.

The new blueberry plant named 'FCE18-015' has not been observed under all possible environmental conditions. The phenotype may vary somewhat with variations in environment and cultural practices such as temperature and light intensity without, however, any variance in genotype.

GENERAL

Classification:
- *Family*.—Ericaceae.
- *Genus*.—*Vaccinium*.
- *Species*.—*Corymbosum*.
- *Common name*.—Southern Highbush Blueberry.

Parentage:
- *Female parent*.—'FL06-556' (U.S. Plant Pat. No. 27,771).
- *Male parent*.—'Ventura' (U.S. Plant Pat. No. 24,606).

Market class: Hand harvest fresh market.

PLANT

General:
- *Plant height*.—1.46 meters.
- *Plant width*.—0.76 meters.
- *Growth habit*.—Upright.
- *Growth*.—Medium to high vigor.
- *Productivity*.—Approximately 4 kg/plant on adult plants.
- *Cold hardiness*.—Not determined, likely USDA zone 7 given southern highbush parentage.
- *Cold tolerance*.—Not determined.
- *Chilling requirement*.—Approximately 0-400 chill hours.
- *Resistance/susceptibility to root rot* (*Phytopthora cinnamomii*).—Not overly susceptible.
- *Resistance/susceptibility to stem blight* (*Botryosphaeria sp.*).—Not overly susceptible.
- *Resistance/susceptibility to Phomopsis twig blight* (*Phomopsis vaccinii*).—Not overly susceptible.
- *Resistance/susceptibility to Botrytis* (*Botrytis cinerea*) .—Not overly susceptible.
- *Resistance/susceptibility to leaf spot* (*Septoria spp.*).—Not overly susceptible.
- *Resistance/susceptibility to leaf rust* (*Naohidemyces vaccinii*).—Not overly susceptible.
- *Resistance/susceptibility to bud mites* (*Acalatus vaccinii*).—Not overly susceptible.
- *Leafing*.—High
- *Twigginess*.—Not twiggy.

STEM

General:
- *Suckering tendency*.—Low.
- *Mature cane color*.—Brush 16-1317.
- *Mature cane length*.—56.1 cm.
- *Mature cane width of* 1 *year old cane*.—5.41 mm.
- *Bark texture*.—Rough.
- *Fall color on new shoots*.—Barn Red 18-1531.
- *Surface texture of new wood*.—Smooth.
- *Internode length on strong, new shoots*.—19.15 mm.
- *Fruiting wood*.—61 cm in length.

FOLIAGE

General:
- *Time of beginning of leaf bud burst*.—December.
- *Leaf color* (*top side*).—Chive 19-0323.
- *Leaf color* (*under side*).—Mosstone 17-0525.

*Leaf arrangement*.—Alternate and distichous.
*Leaf shape*.—Lanceolate (Lindley).
*Leaf margins*.—Entire.
*Undulation of margin*.—Not present.
*Leaf venation*.—Anastomosing and reticulate.
*Leaf apices*.—Acute.
*Leaf bases*.—Obtuse.
*Leaf length*.—65.12 mm.
*Leaf width*.—31.24 mm.
*Leaf length/width ratio*.—Medium.
*Leaf nectarines*.—Absent
*Pubescence of upper side*.—Non pubescent.
*Pubescence of lower side*.—Non pubescent.
*Cross sectional profile*.—Flat.
*Longitudinal profile*.—Plane.
*Attitude*.—Porrect.

Petioles:
*Length*.—3.69 mm.
*Width*.—1.60 mm.
*Color*.—Sweet Pea 15-0531.

FLOWERS

General:
*Time of beginning of flowering*.—December.
*Time of* 50% *anthesis*.—January.
*Flower shape*.—Urceolate.
*Flower bud density*.—Medium.
*Flower fragrance*.—Weak to medium intensity.

Corolla:
*Upper and lower color*.—Snow White 11-0602.
*Length*.—8.73 mm.
*Width*.—6.16 mm.
*Aperture width*.—2.52 mm.
*Anthocyanin coloration of corolla*.—None.
*Corolla ridges*.—Present.
*Protrusion of stigma*.—Does not protrude.

Inflorescence:
*Length*.—23.47 mm
*Diameter*.—29.23 mm.
*Length of peduncle*.—12.89 mm.
*Surface texture of peduncle*.—Non pubescent.
*Color of peduncle*.—Green Oasis 15-0538.
*Length of pedicel*.—6.05 mm.
*Surface texture of pedicel*.—Non pubescent.
*Color of pedicel*.—Green Oasis 15-0538.
*Number of flowers per cluster*.—4 to 7.
*Flower cluster density*.—Medium.

Calyx (with sepals):
*Diameter*.—4.24 mm.
*Color* (*sepals*).—Upper and lower is Spinach Green 16-0439.

Pistil:
*Length*.—8.73 mm.
*Ovary color* (*exterior*).—Peridot 17-0336.
*Style*.—Length — 7.82 mm.

Stamen:
*Length*.—7.41 mm.
*Number per flower*.—10.
*Filament color*.—Hay 12-0418.

Anther:
*Length*.—4.44 mm.
*Number*.—20 (2 per filament).
*Color*.—Adobe 17-1340.

Pollen:
*Abundance*.—Medium-High.
*Color*.—Cornhusk 12-0714.
*Self-compatibility*.—Average.

FRUIT

General:
*Time of fruit ripening*.—Mid March to May.
*Time of* 50% *maturity*.—Second week of April.
*Fruit development period*.—55 days.
*Cluster density*.—3-5 berries per cluster.
*Unripe fruit color*.—Lily Green 13-0317.
*Ripe berry color*.—Dapple Gray 16-3907.
*Berry surface wax abundance*.—High.
*Berry flesh color*.—Pale Star 12-0626.
*Berry weight*.—1.356 g.
*Berry height from calyx to scar*.—12.82 mm.
*Berry diameter*.—17.26 mm.
*Berry shape*.—Slight oblate to round.
*Fruit stem scar*.—1.82 mm.
*Sweetness when ripe*.—Medium.
Firmness when ripe.—350 g/mm average through years (Measured with FirmTech tool).
*Acidity when ripe*.—Medium
*Storage quality*.—High. Good results on evaluations up to 45 and 60 days in cold storage.

SEED

General:
*Seed abundance in fruit*.—Very low.
*Seed color*.—Sierra 18-1239.
*Seed dry weight*.—0.023 g per 100 seeds.
*Seed length*.—1.73 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of new variety ('FCE18-015') |
|---|---|---|---|
| 'Ventura' (U.S. Plant Pat. 24,606) | Storability | 14 to 28 days | High. Good results on evaluations up to 45 and 60 days in the cooler. |
| 'TH-1008' (U.S. Plant Pat. 32,219) | Storability | 28 days | High. Good results on evaluations up to 45 and 60 days in the cooler. |
| 'FL06-556' (U.S. Plant Pat. 27,771) | Storability | 4 weeks | High. Good results on evaluations up to 45 and 60 days in the cooler. |

TABLE 1-continued

| Comparison Table | | | |
|---|---|---|---|
| Denomination of similar variety | Characteristic for comparison | State of expression of similar variety | State of expression of new variety ('FCE18-015') |
| 'FCM12-087' (U.S. Plant Pat. 29,287) | Plant: Vigor | Medium | Medium to High |
| 'FCM12-087' (U.S. Plant Pat. 29,287) | Crop: Production time | Late | Mid |
| 'FCM12-045' (U.S. Plant Pat. 29,468) | Fruit: firmness | Medium | Firm |

The invention claimed is:

1. A new and distinct variety of blueberry plant named 'FCE18-015' substantially as illustrated and described herein.

* * * * *